US011129607B2

(12) United States Patent
Isshiki

(10) Patent No.: US 11,129,607 B2
(45) Date of Patent: Sep. 28, 2021

(54) ANCHORED LOOP-IN-LOOP SUTURE ANCHOR

(71) Applicant: Conmed Corporation, Utica, NY (US)

(72) Inventor: Ryo Isshiki, St. Petersburg, FL (US)

(73) Assignee: Conmed Corporation, Utica, NY (US)

( * ) Notice: Subject to any disclaimer, the term of this patent is extended or adjusted under 35 U.S.C. 154(b) by 155 days.

(21) Appl. No.: 16/003,311

(22) Filed: Jun. 8, 2018

(65) Prior Publication Data

US 2018/0353168 A1 Dec. 13, 2018

Related U.S. Application Data

(60) Provisional application No. 62/518,770, filed on Jun. 13, 2017.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0406* (2013.01);
(Continued)

(58) Field of Classification Search
CPC .......... A61B 17/06166; A61B 17/0401; A61B 2017/0417; A61B 2017/0477; A61B 2017/0414; A61B 2017/06185; A61B 2017/0404; A61B 2017/0445; A61B 2017/0458; A61B 17/0485; A61B 2017/0409; A61B 2017/0496; A61B 2017/0412; A61B 2017/044; A61B 17/0469; A61B 2017/0403; A61B 2017/0475; A61B 2017/0406; A61B 2017/0464; A61B 17/04; A61B 2017/06176; A61B 2017/0459; A61B 2017/06057; A61B 2017/0427;
(Continued)

(56) References Cited

U.S. PATENT DOCUMENTS 3,580,256 A 5/1971 Wilkinson et al.
5,300,078 A * 4/1994 Buelna ............. A61B 17/12013
242/389

(Continued)

FOREIGN PATENT DOCUMENTS

EP 2698117 2/2014

OTHER PUBLICATIONS

Ronald Clousman, M.D. and Nicholas Sgaglione, M.D., Labral Repair, JuggerKnot Soft Anchor brochure, 2010, 2011, 12 pages.
(Continued)

*Primary Examiner* — Katherine M Shi
(74) *Attorney, Agent, or Firm* — Bond, Schoeneck & King, PLLC; Frederick J. M. Price

(57) ABSTRACT

A system and method for securing a target body to a bone mass with a loop-in-loop suture anchor. The system generally includes suture material passing through a substrate (e.g., suture anchor). The suture material includes a splice that allows the suture material to be passed through the splice and around a target body, ultimately creating three loops in the suture material. By tensioning the loops and/or ends of the suture material, the loops bring the target body into a desired position relative to the bone mass and secure it in that position.

19 Claims, 10 Drawing Sheets

(52) U.S. Cl.
CPC .............. *A61B 2017/0417* (2013.01); *A61B 2017/0477* (2013.01)

(58) Field of Classification Search
CPC ........ A61B 17/0466; A61B 2017/0446; A61B 2017/0618; A61B 17/06; A61L 17/00; A61F 2/0811; A61F 2002/0852; A61F 2002/0888; A61F 2002/0882; A61F 2/0805
See application file for complete search history.

(56) References Cited

U.S. PATENT DOCUMENTS

| | | | |
|---|---|---|---|
| 5,540,703 | A | 7/1996 | Barker, Jr. et al. |
| 7,658,751 | B2 | 2/2010 | Stone et al. |
| 8,795,334 | B2 | 8/2014 | Astorino et al. |
| 8,951,286 | B2 | 2/2015 | Sugimoto et al. |
| 9,060,764 | B2 | 6/2015 | Sengun |
| 9,078,651 | B2 | 7/2015 | Astorino et al. |
| 9,314,241 | B2 | 4/2016 | Stone et al. |
| 9,370,352 | B2 | 6/2016 | Astorino et al. |
| 9,402,620 | B2 | 8/2016 | Pilgeram |
| 9,504,462 | B2 | 11/2016 | Dooney, Jr. et al. |
| 9,955,980 | B2 | 5/2018 | Norton et al. |
| 10,265,060 | B2 | 4/2019 | Dooney, Jr. et al. |
| 2008/0255613 | A1* | 10/2008 | Kaiser ............... A61B 17/06166 606/232 |
| 2013/0096612 | A1* | 4/2013 | Zajac ................. A61B 17/0401 606/232 |
| 2013/0296931 | A1* | 11/2013 | Sengun ........... A61B 17/06166 606/228 |
| 2015/0032157 | A1* | 1/2015 | Dooney, Jr. ........ A61B 17/0401 606/232 |
| 2015/0351739 | A1* | 12/2015 | Napolitano ........ A61B 17/0401 606/228 |
| 2017/0049432 | A1* | 2/2017 | Dooney, Jr. ........ A61B 17/0487 |
| 2018/0353166 | A1* | 12/2018 | Breslich ............ A61B 17/0401 |
| 2019/0282283 | A1* | 9/2019 | Dooney ................. A61B 17/04 |

OTHER PUBLICATIONS

European Patent Office Report, EPO Form 2001, Application No. 12 748 076.2, pp. 1-4, dated Mar. 2, 2017.

\* cited by examiner

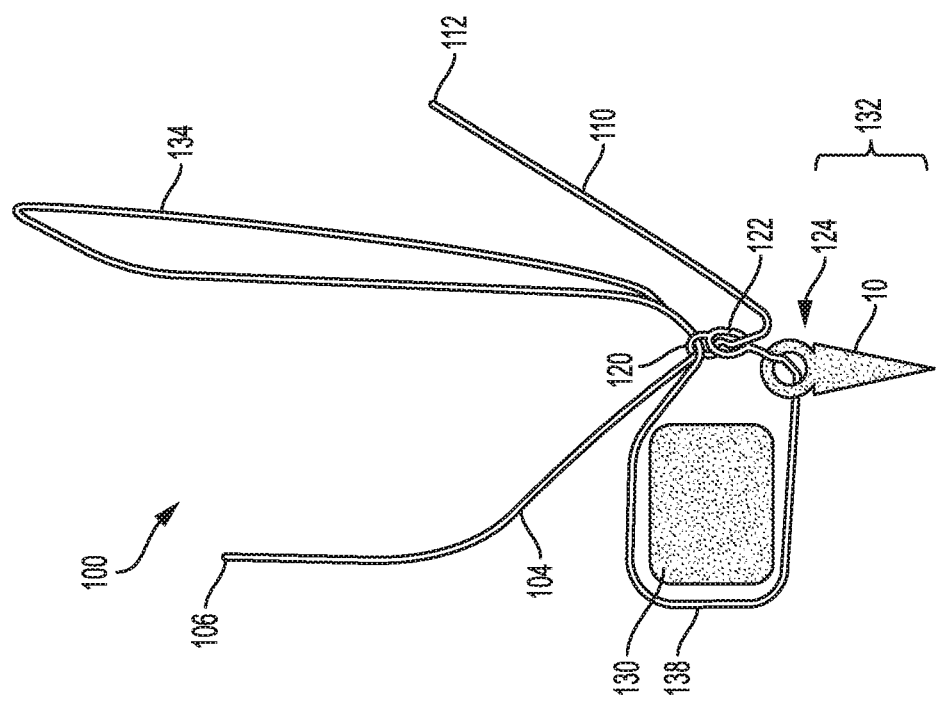
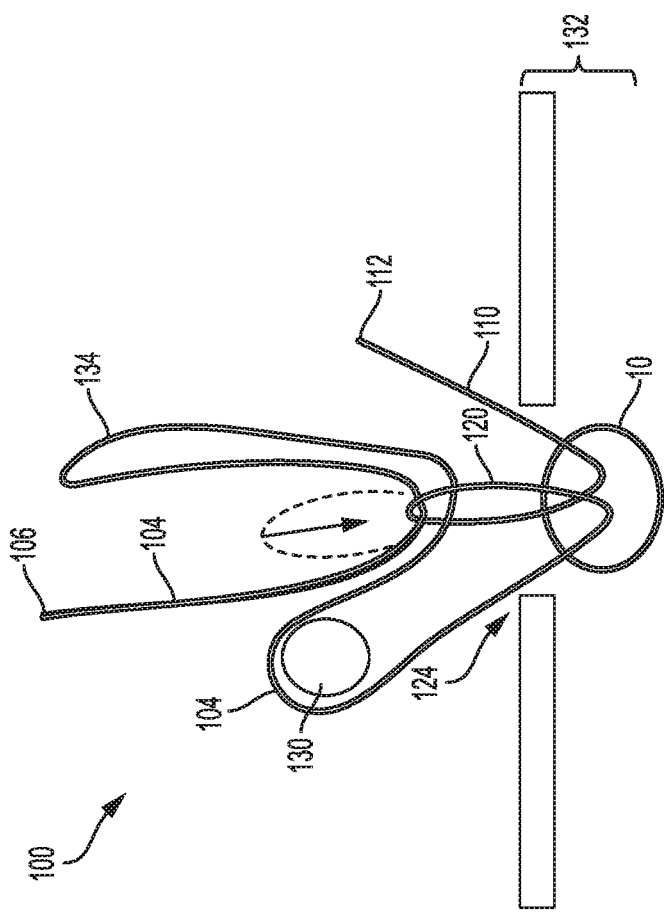
FIG. 8A
FIG. 7B

ANCHORED LOOP-IN-LOOP SUTURE ANCHOR

CROSS-REFERENCE TO RELATED APPLICATION

The present application relates and claims priority to U.S. Provisional Patent Application Ser. No. 62/518,770 filed Jun. 13, 2017, the entirety of which is hereby incorporated by reference.

BACKGROUND OF THE INVENTION

1. Field of the Invention

The invention relates generally to devices for attaching two biological bodies in fixed relation to each other and more particularly, a loop-in-loop suture anchor for securing a tissue to a bone mass.

2. Description of Related Art

Due to the dynamic and complex nature of joint anatomy, injuries in the bone or soft tissue that disrupt the innate interaction between key anatomical features may lead to pathological conditions that require correction through surgery. The objective of these procedures is to restore a biomechanically functional arrangement between key anatomical features within a joint, which may resemble an anatomically healthy joint structure.

A variety of devices is available to facilitate the corrective surgery required by the injuries to the joint anatomy, such as screws, staples, cement, suture anchors, and sutures alone. These devices may be used to attach biological bodies, such as tissue, ligaments, tendons, muscles, bones, prostheses, and grafts, together.

Arthroscopic joint surgery has gained popularity within the field of orthopedics and sports medicine as a less invasive approach to joint repair compared to traditional open surgeries. In this context, suture anchors have also gained popularity as a means of fixation compatible with the inherent complexities and restrictions that come with the spatial constraints of arthroscopic procedures.

In general, as should be understood by a person of ordinary skill in the art in conjunction with a review of this disclosure, a suture anchor is typically comprised of suture material attached to a small anchoring device. The anchoring device, such as a screw, is inserted into a bone mass and fixed in place. After insertion of the anchor, the attached suture is passed through or around the tissue or biological body to be attached.

The process of tying knots around the tissue or biological body is required to establish fixation to the bone mass. However, knot tying is a time consuming process and has clear disadvantages. Conventional knots carry an inherent risk of becoming unraveled prior to the patient healing. Furthermore, the resultant knot stack may irritate the surrounding biological bodies and trigger inflammation. Even more troublesome, the knot stack may cause chronic injury in the joint post-operatively.

Therefore, there is a need for a system and method for fixing tissue or biological bodies onto a bone mass with an easy-to-use, reliable suture anchor device.

SUMMARY OF THE INVENTION

The primary objective of the present invention is to provide an easy-to-use suture construct for reliable fixation of tissue or other biological bodies onto a bone mass when applied to a suture anchor device. Another objective of the present invention is to provide an alternative to conventional knot-tying for the purpose of achieving reliable fixation and to control the formation of a knot structure to minimize unraveling or irritation of the surrounding biological bodies.

The present invention is directed to a loop-in-loop suture construct, inter alia, a system and method for securing a target body to a bone mass with a loop-in-loop suture anchor. In one embodiment, the present invention is a suture construct. The suture construct is a substrate having a suture material passing therethrough. The suture material has a first length terminating at a passing end and a second length terminating at a closing end. A splice is formed in the first length of the suture material and a first loop in the suture material is formed between the passing end and the closing end. The closing end extends through the splice to form the first loop.

In another embodiment, the present invention is a suture construct system. The system includes a substrate having a suture material passing therethrough. The suture material has a first length terminating at a passing end and a second length terminating at a closing end. A splice is formed in the first length of the suture material and a first loop in the suture material is formed between the passing end and the closing end. The closing end extends through the splice to form the first loop. A second loop in the suture material includes a portion of the first length of the suture material which extends through the first loop. A third loop includes the first length of suture material between the splice and the portion of the first length of the suture material extending through the first loop. The third loop extends around a target body.

In one embodiment, the present invention is a method for securing a target body in a position relative to a substrate. The method comprises the steps of: (i) providing a construct having substrate and a suture material having a first length with a passing end and a second length with a closing end, the suture material passing through the substrate at a plurality of passing locations, a splice formed in the first length of the suture material, and a first loop in the suture material formed between the passing end and the closing end, wherein the closing end extends through the splice to form the first loop; (ii) preparing a bone hole; (iii) passing the substrate into the bone hole, the substrate being in an undeployed configuration; (iv) passing the first length of suture material around a target body; (v) passing a portion of the first length of suture material, between the splice and the passing end, around the target body and through the first loop; (vi) pulling the closing end distally from the substrate; (vii) pulling the second loop distally from the substrate; (viii) passing the passing end and the closing end through the second loop and pulling the passing end and the closing end through the second loop; and (ix) pulling the passing end distally from the substrate until the substrate is in the deployed configuration.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

FIG. 7B is another side view schematic representation of the collapse of the first loop of the loop-in-loop suture construct according to an embodiment;

FIG. 8A is a side view schematic representation of the target body positioned in the desired location relative to the substrate of the loop-in-loop suture construct according to an embodiment;

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Filaments and sutures, as the terms are used and described herein, includes braided (i.e., multi-filament) suture and monofilament suture as well as any other metallic or non-metallic filamentary or wire-like material suitable for performing the function of a suture. This material can include both absorbable and non-absorbable materials.

Figure 1A:
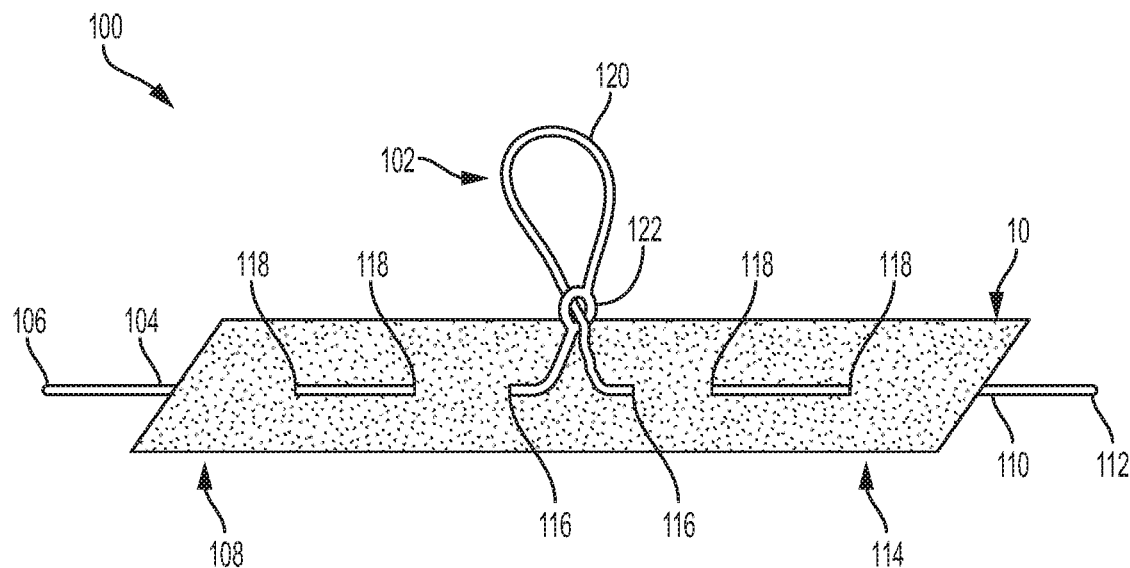
FIG. 1A is a side view schematic representation of a loop-in-loop suture construct in the undeployed configuration according to an embodiment.
Figure 1B:
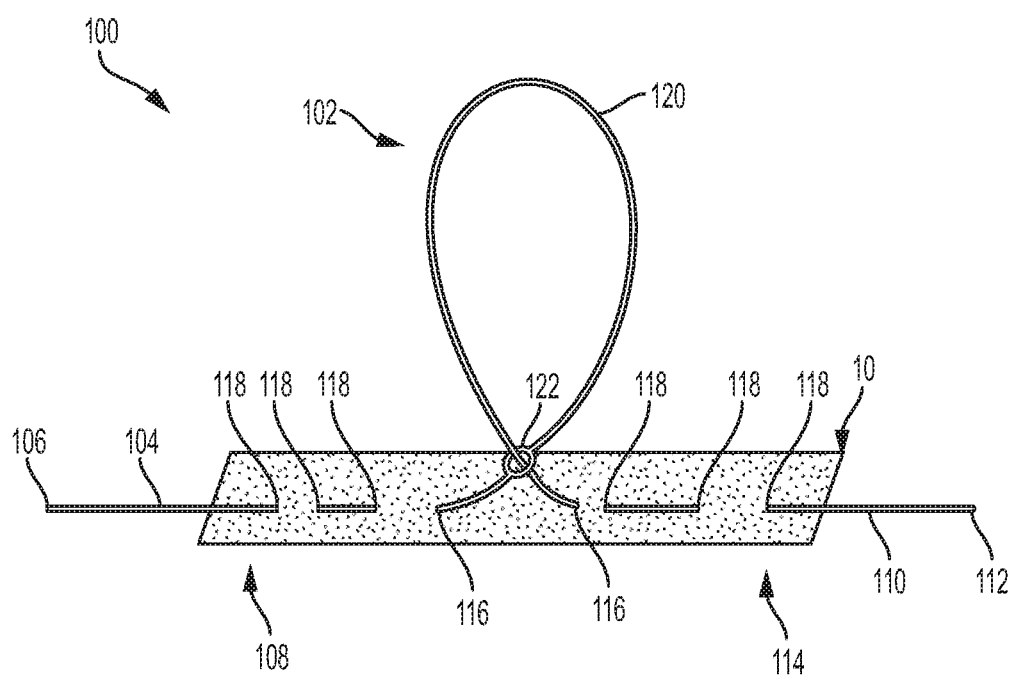
FIG. 1B is another side view schematic representation of a loop-in-loop suture construct in the undeployed configuration according to an embodiment.

Referring now to FIGS. 1A-1B, there are shown side view schematic representations of a loop-in-loop suture construct 100 in the undeployed configuration according to an embodiment. In the depicted embodiment, the loop-in-loop suture construct 100 comprises length of suture 102 and a substrate 10. In the undeployed configuration, as shown in FIGS. 1A-1B, the suture 102 has a first length 104 with a passing end 106 extending from a first side 108 of the substrate 10 and a second length 110 with a closing end 112 extending from a second side 114 of the substrate 10. In the depicted embodiment, the first side 108 opposes the second side 114 such that the first side 108 and the second side 114 extend in opposing directions from a general midpoint of the substrate 10 (i.e., the substrate 10 is comprised of two halves, the first side 108 and the second side 114, if folded in half). Between the first side 108 and second side 114, the suture 102 is woven through the substrate 10 such that there is a plurality of entry/exit points (i.e., passing locations) 116, 118 wherein the suture 102 enters/exits the substrate 10. In one particular embodiment, shown in FIGS. 1A-1B, the plurality of entry/exit points 116, 118 include two central entry/exit points (passing locations) 116 and two or more lateral entry/exit points (passing locations) 118.

As shown in FIGS. 1A-1B, the suture 102 extending between the two central entry/exit points 116 comprises a first loop 120. In the depicted embodiment, the first loop 120 is created by passing the closing end 112 through a splice 122 in the suture 102. The splice 122 shown in FIGS. 1A-1B is created by passing an end 106, 112 of suture 102 through itself prior to weaving the suture 102 through the substrate 10. The first loop 120 is an adjustable loop or a one-way closing loop which may be collapsed by pulling only one of the two ends 106, 112 of suture 102. For example, in the undeployed configuration, pulling the closing end 112 in a direction away from the second side 114 (and the first side 108) collapses the first loop 120. Pulling the passing end 106 in a direction away from the first side 108 (and the second side 114) of the substrate 10 does not collapse the first loop 120.

In another embodiment, the one-way closing loop is replaced with a half-hitch knot or any other knot structure with the same one-way functionality. Further, the one-way closing loop (first loop 120), half-hitch knot, and other similar knots are the least cumbersome and therefore less likely to cause irritation or injury.

Figure 2:
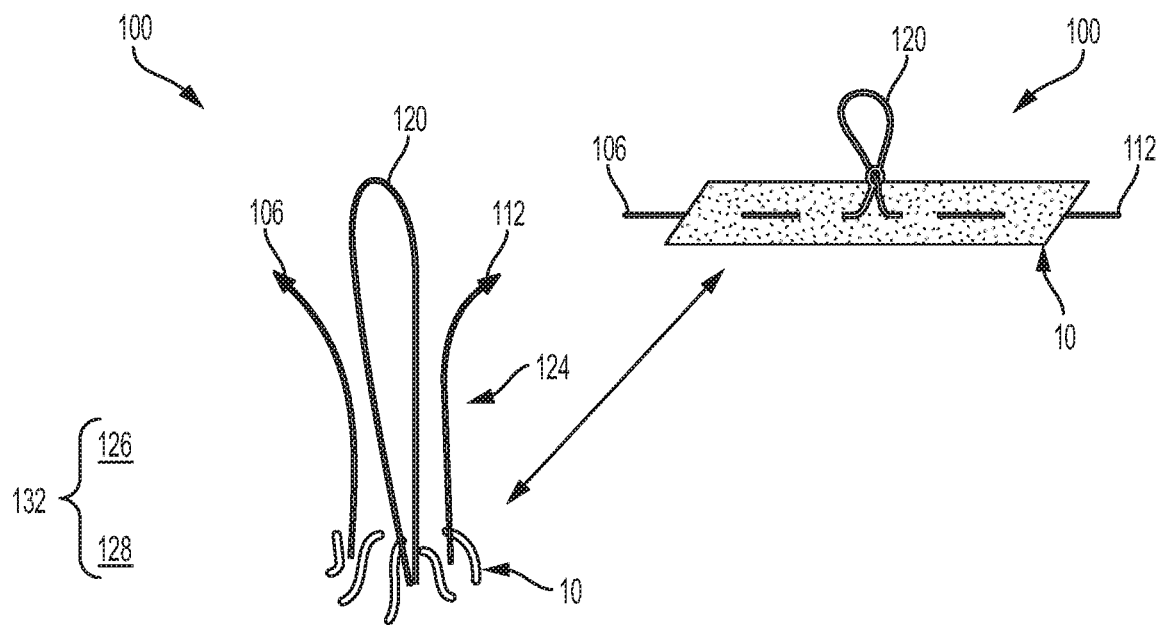
FIG. 2 is a side view schematic representation of a loop-in-loop suture construct, in the undeployed configuration, inserted into a bone hole according to an embodiment.

Turning now to FIG. 2, there is shown a side view schematic representation of a loop-in-loop suture construct 100, in the undeployed configuration, inserted into a bone hole 124 according to an embodiment. The construct 100 is inserted into a bone hole 124 such that the substrate 10 is under the cortical layer 126 of the bone 132. In particular, in the embodiment shown in FIG. 2, the substrate 10 is within the cancellous layer 128 of the bone 132 within the bone hole 124. As also shown in FIG. 2, the construct 100 is inserted into the bone hole 124 such that the first loop 120 and passing and closing ends 106, 112 of suture 102 remain outside the bone hole 124. The first loop 120 and the ends 106, 112 of suture 102 are outside the bone hole 124 so that they may be accessible for manipulation by the user for knot-tying.

Figure 3A:
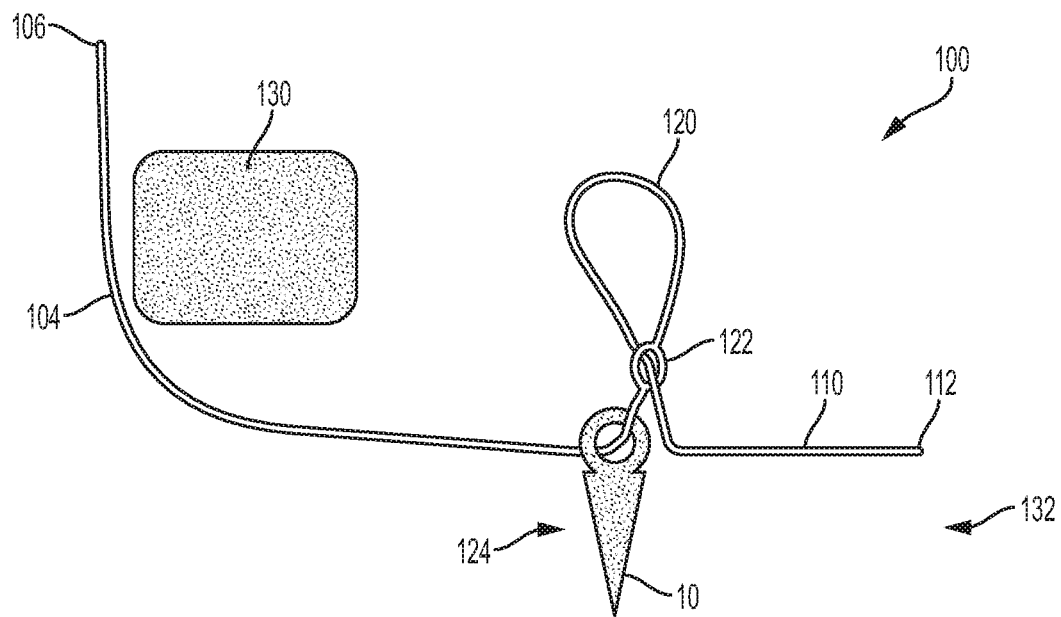
FIG. 3A is a side view schematic representation of a passing end of the loop-in-loop suture construct around a target body according to an embodiment.
Figure 3B:
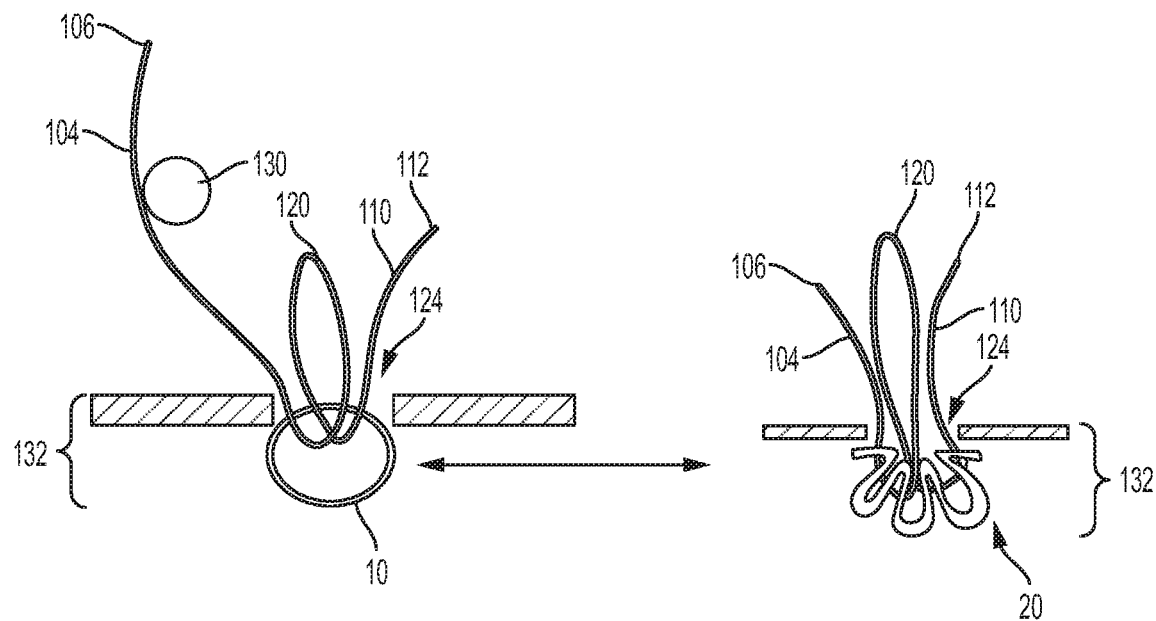
FIG. 3B is another side view schematic representation of a passing end of the loop-in-loop suture construct around a target body according to an embodiment.

Referring now to FIGS. 3A-3B, there are shown side view schematic representations of the passing end 106 of the loop-in-loop suture construct 100 around a target body 130 according to an embodiment. From the undeployed configuration within the bone hole 124, the passing end 106 of the suture 102 is passed through or around a target body 130. In the depicted embodiment, the target body 130 is soft tissue. However, as should be understood by a person of ordinary skill in the art in conjunction with a review of this disclosure, the target body may be any biological body, including, but not limited to, ligaments, tendons, muscles, bones, prostheses, and grafts (which may be fixed upon a bone 132).

Figure 4A:
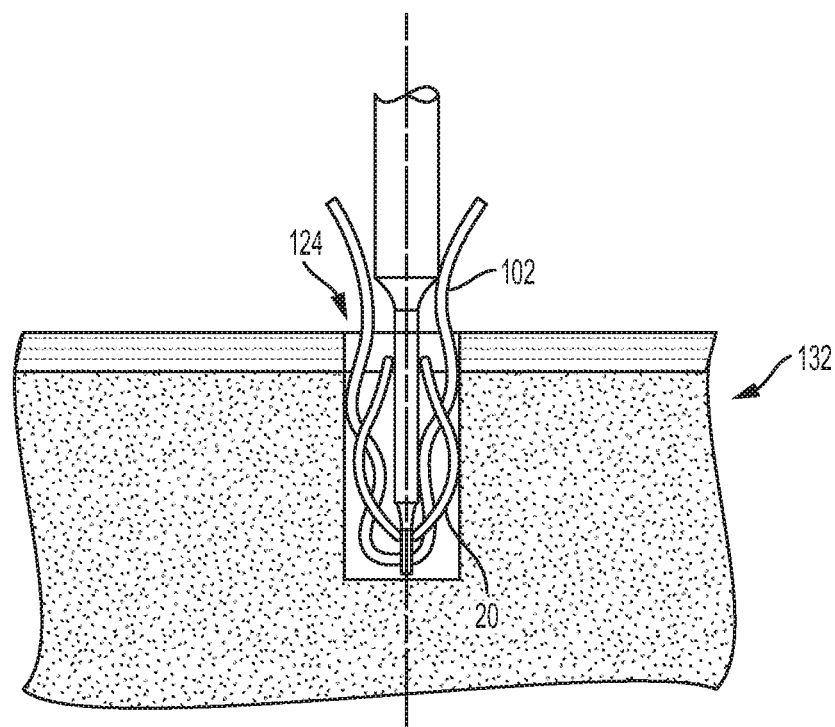
FIG. 4A is a side view schematic representation of an additional embodiment of the substrate in the undeployed configuration.
Figure 4B:
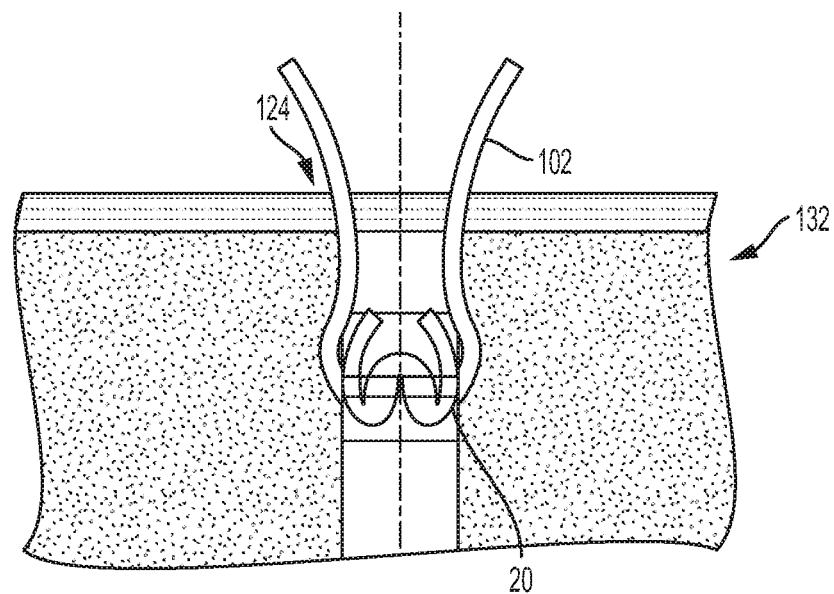
FIG. 4B is a side view schematic representation of the substrate of FIG. 4A shortened and expanded in the deployed configuration.

Turning now to FIGS. 4A-4B, there are shown side view schematic representations of an embodiment of the substrate 10 in the undeployed and deployed configurations. In the depicted embodiment, the substrate 10 is a soft suture anchor 20, such as the Y-KNOT® anchor. One such suture anchor is disclosed in U.S. Pat. No. 9,826,971 assigned to the assignee hereof and incorporated by reference herein in its entirety.

An embodiment of the Y-KNOT® anchor (or soft anchor or "all-suture" anchor) 20 is illustrated in detail in FIGS. 4A-4B. The all suture anchor 20, as shown in FIGS. 4A-4B contains at least two sections: at least one suture 102, which is a suture to be anchored; and an anchor body 20, which is to form a portion of the anchor that can increase in width, thickness and/or diameter and shrink in length as part of deployment. See FIG. 4A, showing the anchor body 20 in the undeployed configuration; and FIG. 4B, showing the anchor body 20 "shortened" and "expanded" in the deployed configuration, which is additive to the increase due to the pleats. This soft anchor embodiment also takes advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening, a material in a first direction causes the material to contract in directions perpendicular to the first direction. Although, it is the anchor body 20 that increases in width, thickness and/or diameter at deployment, it should be understood that the suture 102 can also play a role in the deployment of the anchor even though the suture 102 may remain free (in some embodiments) to slide, and non-slidable in others (at least at a particular position or point in use) in relation to the anchor body 20. The suture 102 helps to position, align and support the anchor body 20, such that if the suture 102 were to be removed from the anchor body 20 after deployment of the anchor, the anchor body 20 may be free to spill (i.e., release), allowing the anchor body 20 to collapse and shrink in size, allowing for easy (and potentially undesirable) removal.

In other words, the anchor body 20 has two primary functions. First, it becomes a base for the suture 102 to slide within. Second, when compressed and/or pleated during deployment, the anchor body 20 becomes more compact in one direction thereby expanding outwardly and increasing its overall width, thickness or diameter to create a retention capacity. This action of having the anchor body 20 change in shape to increase its overall width, thickness or diameter is a useful characteristic which may be used advantageously to secure the anchor in a hole or against a bony or soft tissue. It is this combination of the expanding anchor body 20 coupled with the suture 102 remaining slidable (in some embodiments; and non-slidable in others, at least at a particular position or point in use) in relation to the anchor body 20 that render embodiments of the present invention ideal for the reattachment of soft tissue to bone or soft tissue to soft tissue where it is desirable to pass sliding knots to secure a repair.

Figure 5:
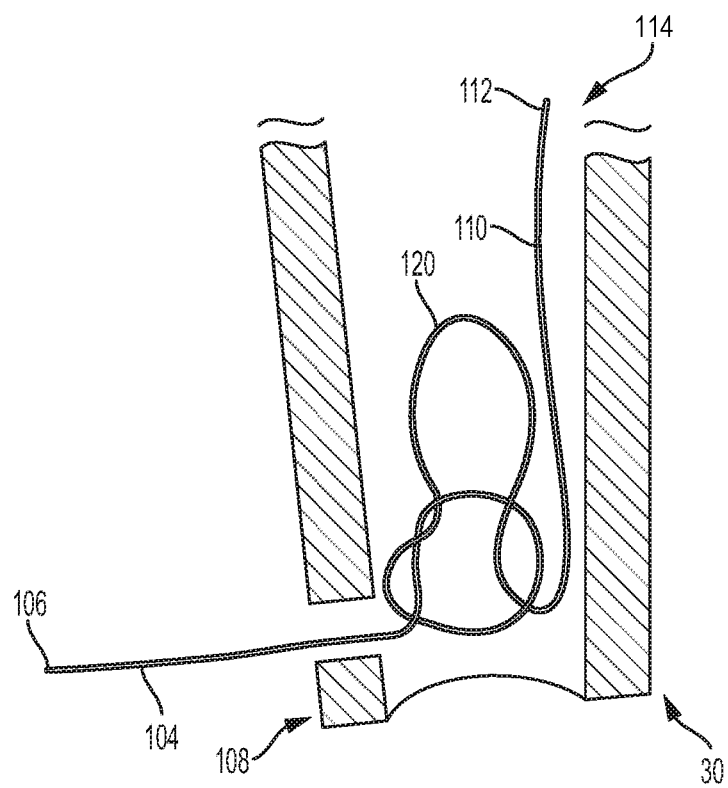
FIG. 5 is a side view schematic representation of another embodiment of the substrate in the undeployed configuration.

Turning briefly to FIG. 5, there is shown a side view schematic representation of another embodiment of the substrate 10 in the undeployed configuration. In another embodiment, the substrate 10 is rigid anchor, such as a PEEK anchor 30. The PEEK anchor 30 may be loaded onto the suture 102 as shown in FIG. 5. The passing end 106 of the first length 104 of suture 102 extends from a first side 108 of the PEEK anchor 30, while the closing end 112 of the second length 110 of suture 102 extends from a second side 114 of the PEEK anchor 30. However, as compared to the substrate 10 shown in FIGS. 1A-1B, the first side 108 and the second side 114 of the PEEK anchor 30 are adjacent and do not oppose each other. Alternative suitable methods for loading the PEEK anchor 30 onto the suture 102 can be used.

Figure 6A:
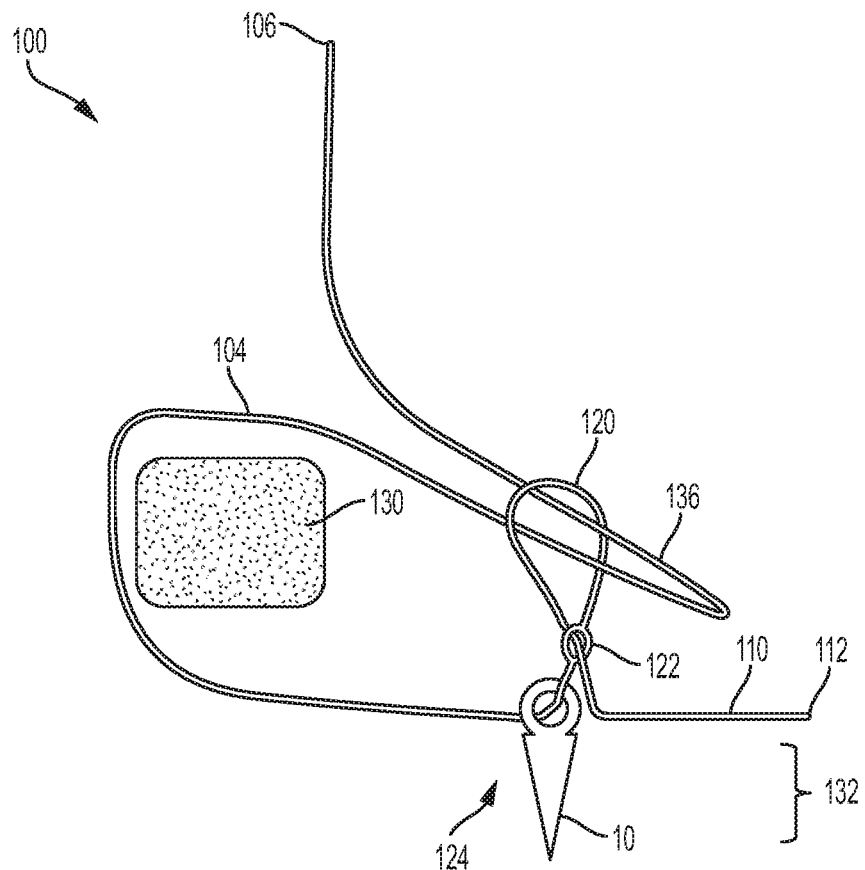
FIG. 6A is a side view schematic representation of the formation of the second loop of the loop-in-loop suture construct according to an embodiment.
Figure 6B:
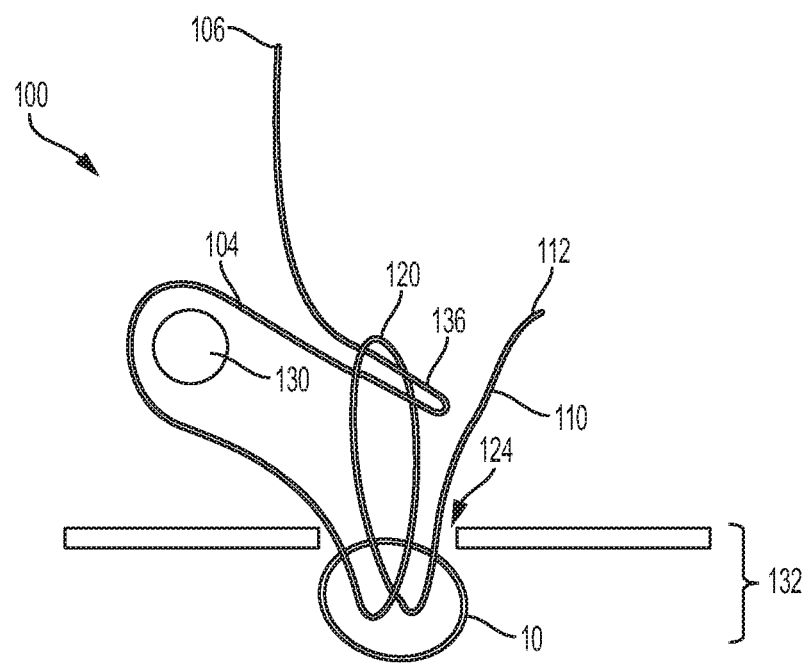
FIG. 6B is another side view schematic representation of the formation of the second loop of the loop-in-loop suture construct according to an embodiment.
Figure 6C:
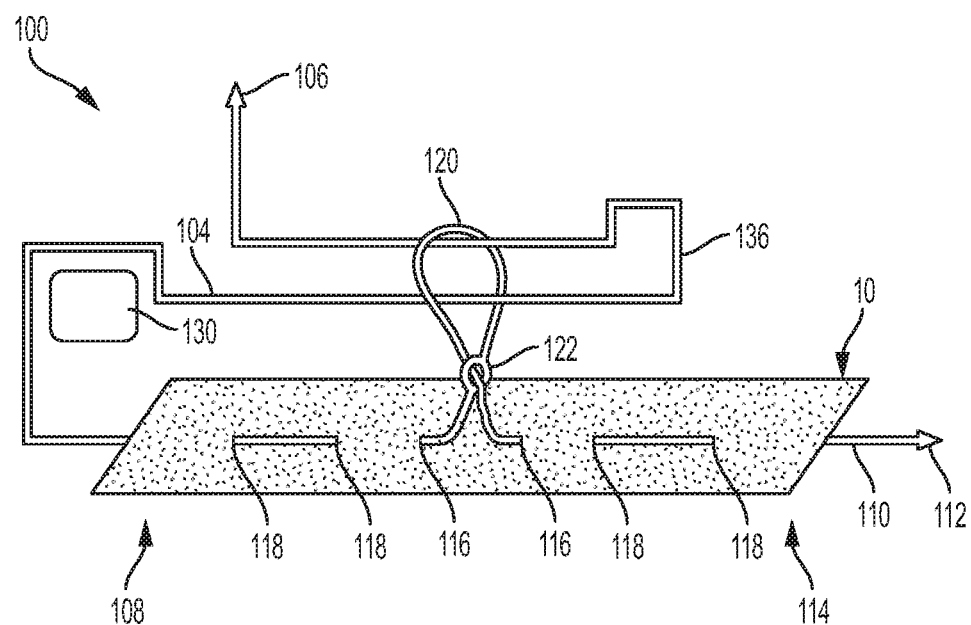
FIG. 6C is an additional side view schematic representation of the formation of the second loop of the loop-in-loop suture construct according to an embodiment.

Referring now to FIGS. 6A-6C, there are shown side view schematic representations of the formation of a second loop 134 of the loop-in-loop suture construct 100 according to an embodiment. In the depicted embodiment, the first length 104 of suture 102 extends around the target body 130. A portion 136 of the first length 104 that extends around the target body 130 is pulled through the first loop 120. However, as shown, the portion 136 of the first length 104 of suture 102 is only pulled through the first loop 120 so much that the passing end 106 of the suture 102 is not pulled through the first loop 120. By passing the portion 136 of the first length 104 of suture 102 through the first loop 120, the second loop 134 is created (see, e.g., FIG. 7A).

Figure 7A:
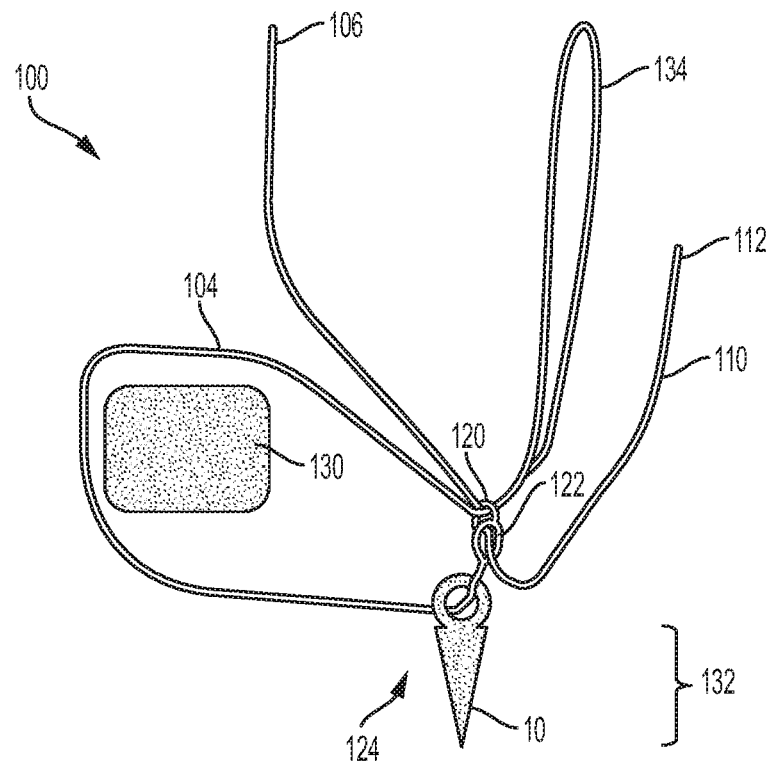
FIG. 7A is a side view schematic representation of the collapse of the first loop of the loop-in-loop suture construct according to an embodiment.

Turning now to FIGS. 7A-7B, there are shown side view schematic representations of the collapse of the first loop 120 of the loop-in-loop suture construct 100 according to an embodiment. As described above, the second loop 134 is created when the portion 136 of the first length 104 of suture 102 is passed through the first loop 120. In the depicted embodiment, the closing end 112 of the second length 110 of suture 102 is pulled to collapse the first loop 120. The term "collapse" or "collapsing" with regard to first loop 120, describes a decrease in the size of a diameter of the first loop 120. For example, as shown in FIGS. 7A-7B, when the closing end 112 is pulled, the first loop 120 collapses and the diameter of the first loop 120 decreases as the second length 110 of suture 102 is elongated. However, it is important to note that the first loop 120 is not entirely collapsed such that the suture 102 may slide within and from the first loop 120.

Still referring to FIGS. 7A-7B, collapsing the first loop 120 forms a third loop 138 around the target body 130 (see, e.g., FIG. 8A). As shown, the third loop 138 is formed from the first length 104 of suture 102. In the depicted embodiment, the second loop 134 and the third loop 138 are opposing sides of the substrate 10; however, the second loop 134 and the third loop 138 may be positioned and located in any configuration relative to each other and the substrate 10 suitable for the surgical procedure.

Figure 8B:
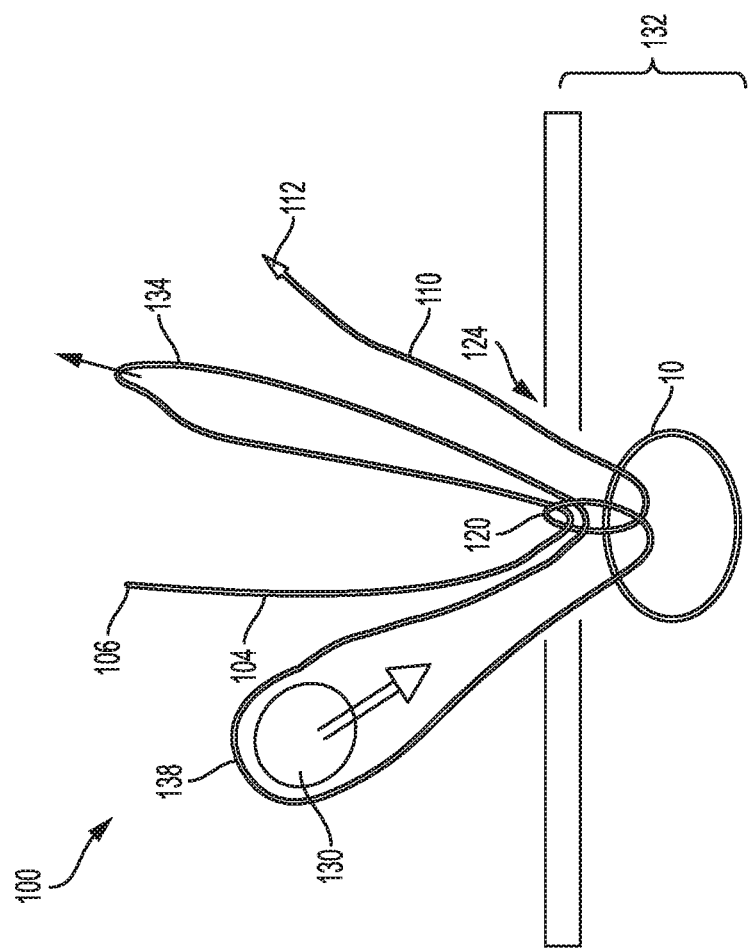
FIG. 8B is another side view schematic representation of the target body positioned in the desired location relative to the substrate of the loop-in-loop suture construct according to an embodiment.

Turning now to FIGS. 8A-8B, there are shown side view schematic representations of the target body 130 positioned in the desired location relative to the substrate 10 of the loop-in-loop suture construct 100 according to an embodiment. As recited above, the first loop 120 is not entirely collapsed. Therefore, the first length 104 of suture 102 may be pulled through the first loop 120. In FIGS. 8A-8B, after the first loop 120 is collapsed, the second loop 134 is pulled to bring the target body 130 closer to the substrate 10. As shown in the depicted embodiment, the second loop 134 is pulled away (i.e., distally) from the substrate 10. In particular, the second loop 134 is pulled away from the substrate 10 substantially in line or parallel with the bone hole 124.

Figure 9A:
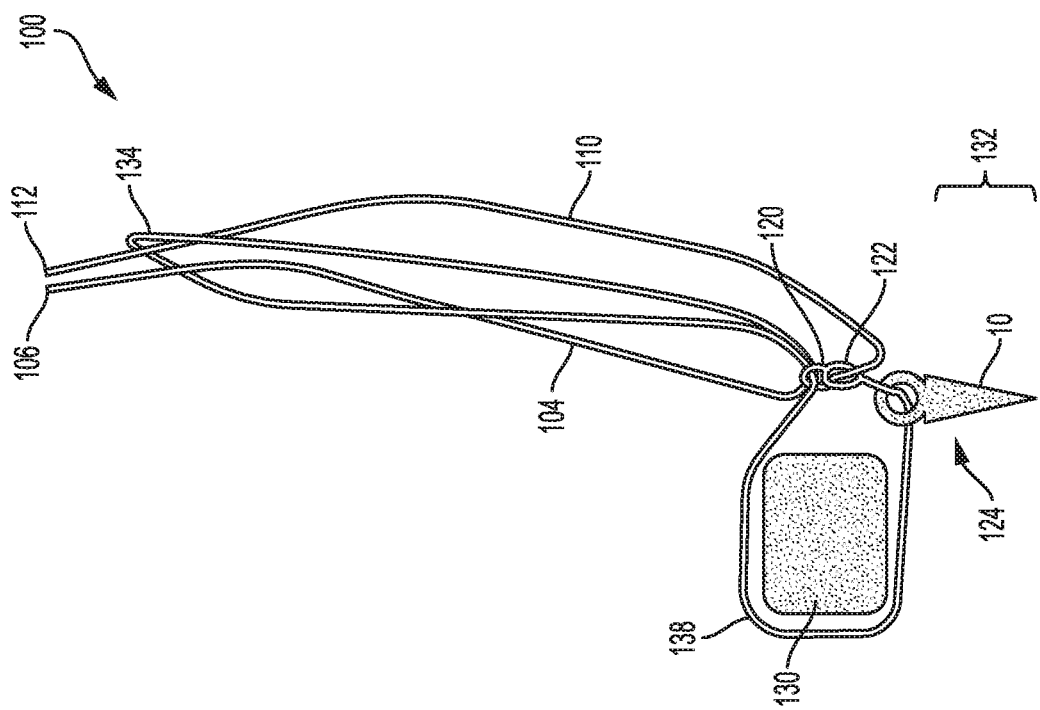
FIG. 9A is a side view schematic representation of the passing end and closing end of suture 102 passed through the second loop of the loop-in-loop suture construct according to an embodiment.
Figure 9B:
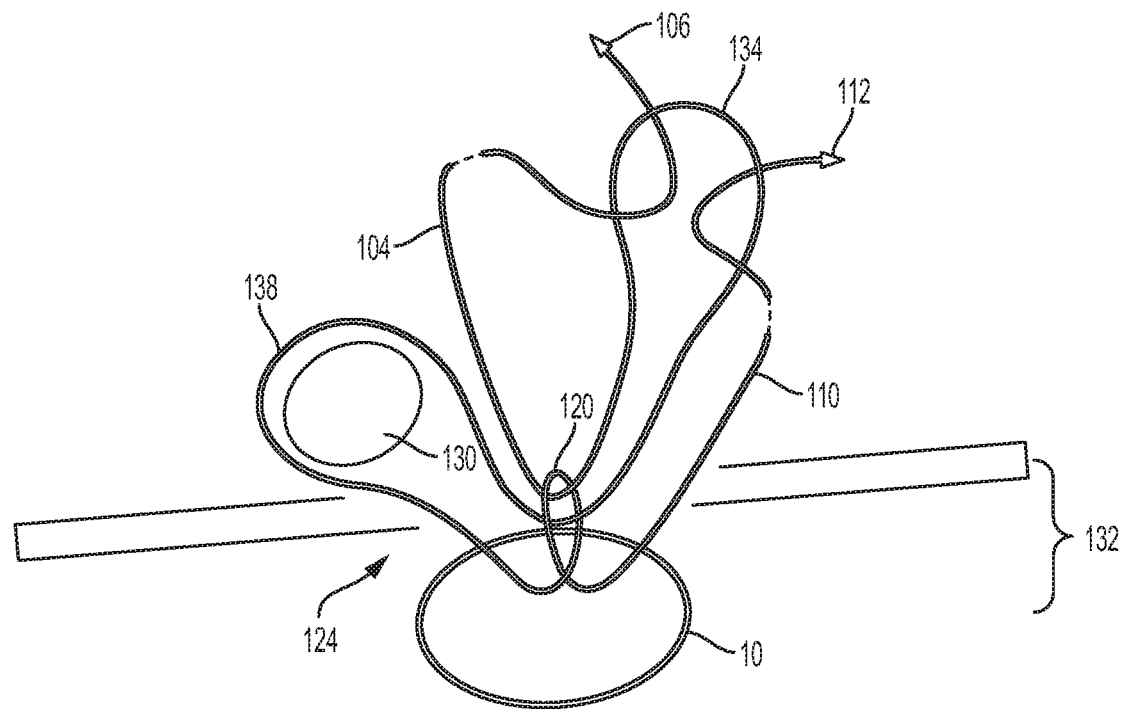
FIG. 9B is another side view schematic representation of the passing end and closing end of suture 102 passed through the second loop of the loop-in-loop suture construct according to an embodiment.
Figure 9C:
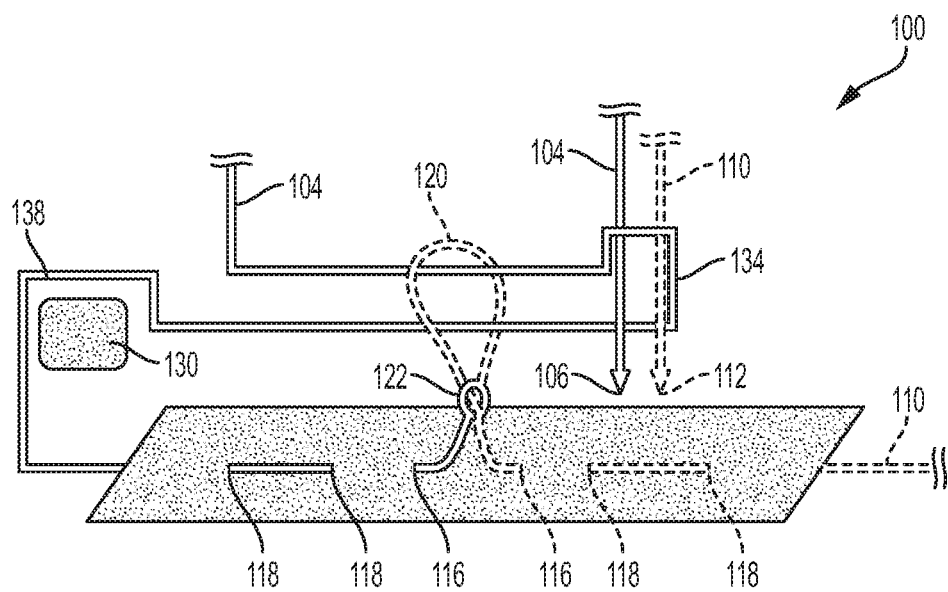
FIG. 9C is an additional side view schematic representation of the passing end and closing end of suture 102 passed through the second loop of the loop-in-loop suture construct according to an embodiment.

Referring now to FIGS. 9A-9C, there are shown side view schematic representations of the passing end 106 and closing end 112 of suture 102 passed through the second loop 134 of the loop-in-loop suture construct 100 according to an embodiment. In the depicted embodiment, the second loop 134 has been pulled distally in order to pull the third loop 138 closer to the substrate 10. In other words, pulling the second loop 134 has decreased a diameter of the third loop 138, as shown clearly in FIGS. 9A-9B. At this step, the second loop 134 is pulled until the target body 130 is in the desired or appropriate position relative to the substrate 10 for the particular surgical procedure. In the depicted embodiment, the target body 130 can be soft tissue and the substrate 10 can be an anchor (e.g., the Y-KNOT® anchor shown in FIGS. 4A-4B) in a bone hole 124. Thus, the second loop 134 is pulled until the soft tissue 130 is pulled to the desired location relative to the anchor 10 and the bone hole 124.

Figure 10:
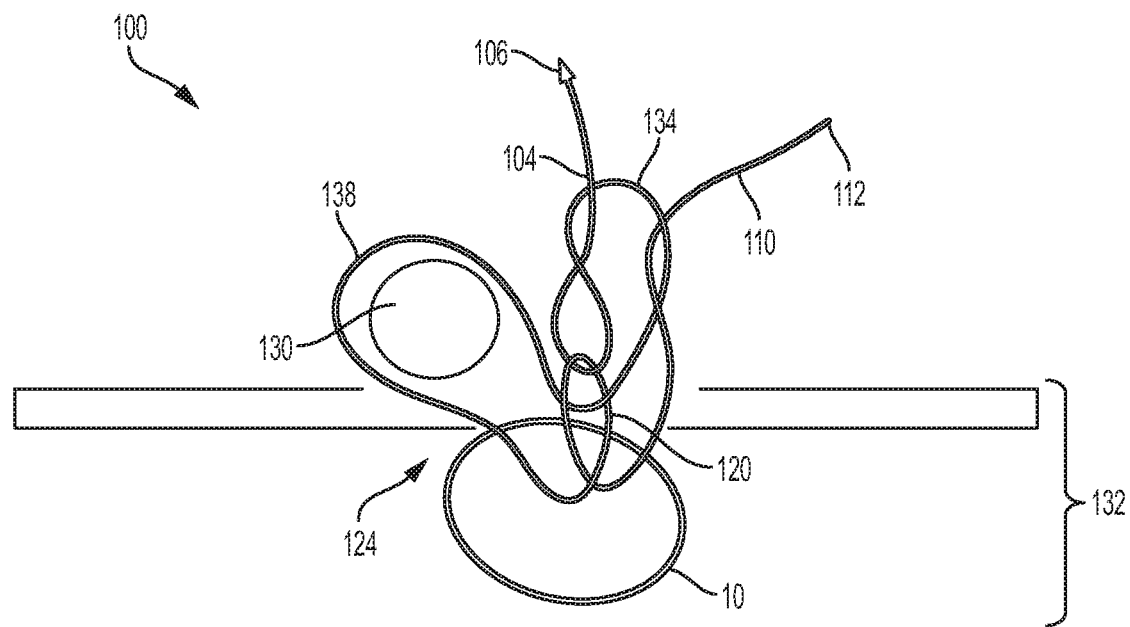
FIG. 10 is a side view schematic representation of the collapse of the second loop of the loop-in-loop suture construct according to an embodiment.

Turning now to FIG. 10, there is shown a side view schematic representation of the collapse of the second loop 134 of the loop-in-loop suture construct 100 according to an embodiment. In the depicted embodiment, the passing end 106 and the closing end 112 are passed through the second loop 134. Thereafter, the passing end 106 is pulled to collapse the second loop 134. The term "collapse" or "collapsing" with regard to second loop 134, describes a decrease in the size of a diameter of the second loop 134. As the passing end 106 is pulled, a diameter of the second loop 134 decreases around the first and second lengths 104, 110 of suture 102 and the first length 104 of suture 102 elongates.

Figure 11:
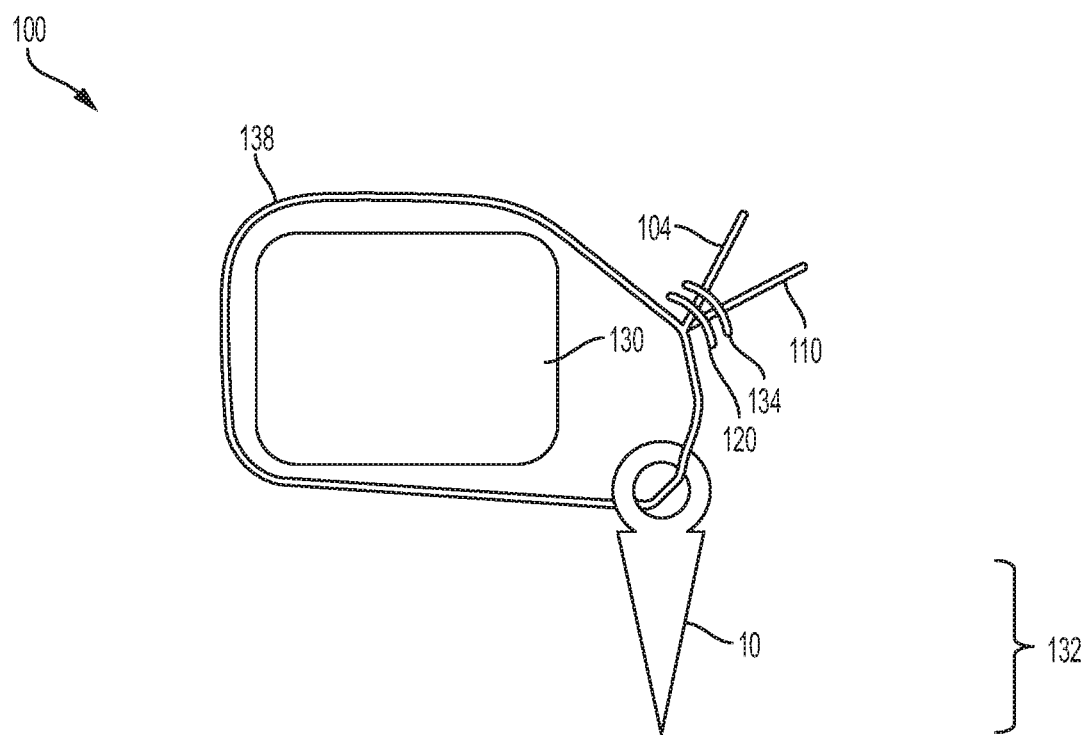
FIG. 11 is a side view schematic representation of the loop-in-loop suture construct in the deployed configuration according to an embodiment.

Referring now to FIG. 11, there is shown a side view schematic representation of the loop-in-loop suture construct 100 in the deployed configuration according to an embodiment. As shown, the second loop 134 and the first loop 120 are collapsed around the first and second lengths 104, 110 of suture 102. Accordingly, the target body 130 is fixed in a position relative to the substrate 10. To decrease irritation at the surgical site, the passing end 106 and the closing end 112 of suture 102 can be trimmed such that only minimal portions of the first and second 104, 110 lengths of suture 102 remain, as shown.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A suture anchor construct, comprising:
    a substrate having a suture material passing therethrough, the suture material having a first length terminating at a passing end and a second length terminating at a closing end;
    a splice formed in the first length of the suture material;
    a first loop in the suture material formed between the passing end and the closing end;
    wherein the closing end extends through the splice to form the first loop and the splice is the only pass-through of the suture material through the suture material;
    a second loop in the suture material formed in the first length of the suture material;
    wherein the second loop is formed in a portion of the first length of the suture material between the passing end and the splice, the portion extending through the first loop and the first loop extending around the portion; and
    wherein in the undeployed configuration, the second loop has a first diameter and in a deployed configuration, the second loop has a second diameter, which is less than the first diameter.

2. The suture anchor construct of claim 1, further comprising a third loop in the suture material formed in the first length of the suture material.

3. The suture anchor construct of claim 2, wherein the third loop in the suture material is formed in the first length of suture material between the splice and the portion of the first length of the suture material extending through the first loop.

4. The suture anchor construct of claim 1, wherein the suture material passes through the substrate at a plurality of passing locations.

5. The suture anchor construct of claim 4, wherein the plurality of passing locations comprise two central passing locations and at least one lateral passing location adjacent each central passing location, and the first loop extends between the two central passing locations.

6. The suture anchor construct of claim 1, wherein in an undeployed configuration, the first loop has a first diameter and in a deployed configuration, the first loop has a second diameter, which is less than the first diameter.

7. The suture anchor construct of claim 1, wherein the substrate is a soft suture anchor or a rigid suture anchor.

8. A suture construct system, comprising:
a substrate having a suture material passing therethrough, the suture material having a first length terminating at a passing end and a second length terminating at a closing end;
a splice formed in the first length of the suture material;
a first loop in the suture material formed between the passing end and the closing end;
wherein the closing end extends through the splice to form the first loop, and the splice is the only pass-through of the suture material through the suture material;
a second loop in the suture material formed in the first length of the suture material;
wherein the second loop is formed in a portion of the first length of the suture material between the passing end and the splice, the portion extending through the first loop and the first loop extending around the portion;
a third loop comprising the first length of suture material between the splice and the portion of the first length of the suture material extending through the first loop;
wherein the third loop is configured to extend around a target body.

9. The system of claim 8, wherein the passing end and the closing end extend through the second loop.

10. The system of claim 8, wherein in an undeployed configuration, the target body is a first distance from the substrate and in a deployed configuration, the target body is a second distance from the substrate, which is smaller than the first distance.

11. A method for securing a target body in a position relative to a substrate, the method comprising the steps of:
providing a construct having the substrate and a suture material having a first length with a passing end and a second length with a closing end, the suture material passing through the substrate at a plurality of passing locations, a splice formed in the first length of the suture material such that the splice is the only pass-through of the suture material through the suture material, and a first loop in the suture material formed between the passing end and the closing end, wherein the closing end extends through the splice to form the first loop;
preparing a bone hole; and
passing the substrate into the bone hole, the substrate being in an undeployed configuration;
wherein the first loop extends from the substrate in the bone hole with the first length of the suture material and the second length of the suture material extending from the bone hole on opposing sides of the first loop.

12. The method of claim 11, further comprising the step of passing the first length of suture material around a target body.

13. The method of claim 12, further comprising the step of passing a portion of the first length of suture material, between the splice and the passing end, around the target body and through the first loop.

14. The method of claim 13, further comprising the step of pulling the closing end distally from the substrate.

15. The method of claim 14, further comprising the step of pulling the second loop distally from the substrate.

16. The method of claim 15, further comprising the steps of:
passing the passing end and the closing end through the second loop; and
pulling the passing end and the closing end through the second loop.

17. The method of claim 16, further comprising the step of pulling the passing end distally from the substrate until the substrate is in a deployed configuration.

18. A suture anchor construct, comprising:
a substrate having a suture material passing therethrough, the suture material having a first length terminating at a passing end and a second length terminating at a closing end;
a splice formed in the first length of the suture material;
a first loop in the suture material formed between the passing end and the closing end;
wherein the closing end extends through the splice to form the first loop and the splice is the only pass-through of the suture material through the suture material;
a second loop in the suture material formed in the first length of the suture material;
wherein the second loop is formed in a portion of the first length of the suture material between the passing end and the splice, the portion extending through the first loop and the first loop extending around the portion; and
a third loop in the suture material formed in the first length of the suture material, wherein the third loop is formed in the first length of suture material between the splice and the portion of the first length of the suture material extending through the first loop.

19. A suture anchor construct, comprising:
a substrate having a suture material passing therethrough, the suture material having a first length terminating at a passing end and a second length terminating at a closing end;
a splice formed in the first length of the suture material;
a first loop in the suture material formed between the passing end and the closing end;
wherein the closing end extends through the splice to form the first loop and the splice is the only pass-through of the suture material through the suture material;
a second loop in the suture material formed in the first length of the suture material;
wherein the second loop is formed in a portion of the first length of the suture material between the passing end and the splice, the portion extending through the first loop and the first loop extending around the portion;
wherein the suture material passes through the substrate at a plurality of passing locations; and
wherein the plurality of passing locations comprise two central passing locations and at least one lateral passing location adjacent each central passing location, and the first loop extends between the two central passing locations.

* * * * *